(12) United States Patent
Kaplan et al.

(10) Patent No.: US 11,964,269 B2
(45) Date of Patent: Apr. 23, 2024

(54) LABORATORY ON LOCATION TEST SYSTEM FOR ACCREDITATION OF BREATHING AIR QUALITY

(71) Applicant: Industrial Technologies and Services, LLC, Davidson, NC (US)

(72) Inventors: Lawrence Kaplan, Miami Lakes, FL (US); Liev Aleman, Miami Lakes, FL (US)

(73) Assignee: Industrial Technologies and Services, LLC, Davidson, NC (US)

( * ) Notice: Subject to any disclaimer, the term of this patent is extended or adjusted under 35 U.S.C. 154(b) by 0 days.

(21) Appl. No.: 17/828,434

(22) Filed: May 31, 2022

(65) Prior Publication Data

US 2022/0297110 A1 Sep. 22, 2022

Related U.S. Application Data

(63) Continuation of application No. 17/355,859, filed on Jun. 23, 2021, now Pat. No. 11,344,876, which is a
(Continued)

(51) Int. Cl.
*B01L 1/00* (2006.01)
*G01N 33/00* (2006.01)
*G16H 40/67* (2018.01)

(52) U.S. Cl.
CPC ............ *B01L 1/52* (2019.08); *G01N 33/0006* (2013.01); *G01N 33/0016* (2013.01);
(Continued)

(58) Field of Classification Search
CPC .............................. B01L 1/52; G01N 33/0009
See application file for complete search history.

(56) References Cited

U.S. PATENT DOCUMENTS 4,287,764 A * 9/1981 Staab ..................... G01D 11/24
73/431
4,324,146 A * 4/1982 Born ....................... G01N 1/24
73/863.12
(Continued)

FOREIGN PATENT DOCUMENTS

DE 4438077 A1 * 5/1996 ......... G01N 33/1806

OTHER PUBLICATIONS

ESPACENET Machine Translation of DE 4438077 A1 Which Originally Published On May 2, 1996. (Year: 1996).*

*Primary Examiner* — David A. Rogers
(74) *Attorney, Agent, or Firm* — Kevin E. West; Advent, LLP

(57) ABSTRACT

A breathing air laboratory on location gas sample test and data collecting system and method, at a remote breathing air provider's facility, that includes an air compressor, for remotely testing, collecting, and monitoring the quality and purity of the breathing air being produced at the provider's facility, that allows an accredited independent monitoring, testing, and analyzing facility to provide breathing air validation and certification to a cloud-based air quality test and analysis account belonging to the breathing air provider facility at any time. The system includes redundant gas sample air sensors for O2 and CO to ensure quality and accuracy in the breathing air test and data collection, and analysis and a "canary" gas sample test module securely mounted in a laboratory chassis, but manually swappable, to ensure credibility and accuracy of the sensors being used to test gas/air samples.

15 Claims, 5 Drawing Sheets

Related U.S. Application Data continuation of application No. 17/076,211, filed on Oct. 21, 2020, now Pat. No. 11,045,800.

(52) U.S. Cl.
CPC ..... *G01N 33/0021* (2013.01); *G01N 33/0031* (2013.01); *G01N 33/004* (2013.01); *G16H 40/67* (2018.01)

(56) References Cited

U.S. PATENT DOCUMENTS

| | | | | |
|---|---|---|---|---|
| 4,459,266 A * | 7/1984 | Lamoreaux | .......... | G01N 31/223 128/204.22 |
| 4,670,223 A * | 6/1987 | Delachapelle | ........ | A61M 16/10 422/4 |
| 5,437,199 A * | 8/1995 | Kaplan | ............ | B63C 11/18 73/863.57 |
| 5,538,690 A * | 7/1996 | Greer | ............ | G01N 21/783 73/31.03 |
| 5,571,948 A * | 11/1996 | Kaplan | ............ | G01N 1/22 422/86 |
| 5,711,916 A * | 1/1998 | Riggs | ............ | B01L 1/52 422/89 |
| 5,746,976 A * | 5/1998 | Yamada | ............ | H05K 7/1411 422/549 |
| 5,965,887 A * | 10/1999 | Patton | ............ | G01N 21/274 250/339.09 |
| 6,287,519 B1 * | 9/2001 | Nordman | ............ | G01N 1/2252 73/23.31 |
| 6,386,014 B1 * | 5/2002 | Butch | ............ | G01N 33/225 73/23.35 |
| 6,522,976 B2 | 2/2003 | Shiba | ............ | G01N 35/026 702/182 |
| 6,631,333 B1 * | 10/2003 | Lewis | ............ | G01N 33/0075 977/959 |
| 6,701,773 B2 | 3/2004 | Rabenecker | ............ | G01N 33/0062 73/23.2 |
| 6,790,178 B1 * | 9/2004 | Mault | ............ | G06F 1/1632 128/920 |
| 6,886,421 B2 * | 5/2005 | Mathur | ............ | G01N 35/1002 73/864.81 |
| 7,089,780 B2 * | 8/2006 | Sunshine | ............ | G01N 33/0073 340/541 |
| 7,183,115 B1 * | 2/2007 | Lauglin | ............ | G01N 33/0073 436/60 |
| 7,201,179 B2 * | 4/2007 | Barr | ............ | G05D 11/135 137/255 |
| 7,366,624 B2 * | 4/2008 | Wobschall | ............ | G01D 3/022 73/1.06 |
| 7,369,945 B2 * | 5/2008 | Miller | ............ | G01N 27/626 340/870.07 |
| 7,617,063 B2 * | 11/2009 | Tiegs | ............ | H04L 67/125 702/108 |
| RE41,946 E * | 11/2010 | Anderson | ............ | G16H 40/63 205/792 |
| 8,117,886 B2 * | 2/2012 | Rolff | ............ | G01M 3/207 73/40 |
| 8,734,720 B2 * | 5/2014 | Nichols | ............ | B01L 9/02 422/65 |
| 8,795,593 B2 * | 8/2014 | Nichols | ............ | G01N 35/04 422/65 |
| 8,847,602 B2 * | 9/2014 | Wittmer | ............ | G01N 27/286 204/422 |
| 8,871,149 B2 * | 10/2014 | Zilioli | ............ | G01N 30/88 422/89 |
| 9,010,173 B2 * | 4/2015 | Lee | ............ | G01N 33/0032 73/31.03 |
| 9,134,284 B1 * | 9/2015 | Laughlin | ............ | G01N 33/0073 |
| 9,763,724 B2 * | 9/2017 | Konesky | ............ | A61B 18/042 |
| 9,926,872 B2 * | 3/2018 | Makled | ............ | B60W 20/10 |
| 9,974,918 B2 * | 5/2018 | Armstrong | ............ | A61M 16/0677 |
| 10,031,095 B2 * | 7/2018 | Hill | ............ | G01N 27/16 |
| 10,124,196 B2 * | 11/2018 | Roberts | ............ | F24F 8/10 |
| 10,161,923 B1 * | 12/2018 | Laughlin | ............ | G01N 33/0006 |
| 10,179,308 B2 * | 1/2019 | Schaeffer | ............ | G05B 19/406 |
| 10,318,441 B2 * | 6/2019 | Inoue | ............ | G01N 33/0037 |
| 10,376,844 B2 * | 8/2019 | Adhikari | ............ | G01N 15/082 |
| 10,561,863 B1 * | 2/2020 | Dashevsky | ............ | A61B 5/01 |
| 10,610,134 B2 * | 4/2020 | Burnett | ............ | A61B 5/14507 |
| 10,921,221 B2 * | 2/2021 | Mou | ............ | G01N 33/0047 |
| 11,045,800 B1 * | 6/2021 | Kaplan | ............ | G01N 33/0006 |
| 2002/0095951 A1 * | 7/2002 | Ha | ............ | F25J 3/04636 62/643 |
| 2003/0216869 A1 * | 11/2003 | Sunshine | ............ | H04L 67/125 702/22 |
| 2006/0281101 A1 * | 12/2006 | Dzenitis | ............ | G01N 35/00 435/7.1 |
| 2012/0000462 A1 * | 1/2012 | Edwards | ............ | A61M 16/204 128/204.22 |
| 2012/0266889 A1 * | 10/2012 | Roberts | ............ | F24F 8/167 128/205.27 |
| 2015/0068518 A1 * | 3/2015 | Roberts | ............ | A62B 9/006 128/205.24 |
| 2016/0362321 A1 * | 12/2016 | Robertson | ............ | C02F 3/30 |
| 2017/0089598 A1 * | 3/2017 | Wallace | ............ | F24F 11/86 |
| 2017/0236397 A1 * | 8/2017 | Myslenski | ............ | H04N 7/183 348/143 |
| 2019/0035253 A1 * | 1/2019 | Jones, II | ............ | H04Q 9/02 |
| 2020/0088618 A1 * | 3/2020 | Voight | ............ | G01N 35/00871 |
| 2022/0339391 A1 * | 10/2022 | Gillerman | ............ | A61M 16/022 |

\* cited by examiner

LABORATORY ON LOCATION TEST SYSTEM FOR ACCREDITATION OF BREATHING AIR QUALITY

CROSS REFERENCE TO RELATED APPLICATIONS

This application is a continuation of U.S. patent application Ser. No. 17/076,211, filed on Oct. 21, 2020.

BACKGROUND OF THE INVENTION

1. Field of the Invention

This invention provides a breathing air and gas purity and quality test system, including a laboratory on location at the breathing air provider's facility, for accredited analysis by an independent accredited monitoring laboratory, of the purity, quality, and safety of the provider's breathing air output equipment.

The laboratory on location gas sample test system includes a swappable, "canary" gas sensor-filled module to ensure accurate quality sensor calibration and redundant, specific gas sensors for increased accuracy and reliability in the gas sample test results. Breathing air and gas sample test data are digitally processed and stored in the "canary" gas sample test module. A communication device, such as a laptop or tablet, can receive the gas sample test data from the canary gas sample test module and transmit the gas sample data over the Internet to an independent, accredited gas quality monitoring laboratory for round-the-clock gas sample testing, analysis, and quality evaluation. A cloud-based portal maintained by the independent accredited gas quality monitoring laboratory provides accessibility by the breathing air provider for its gas sample analysis and accreditation.

2. Description of the Prior Art

Governmental and other overseeing agencies, that assure gas and air purity, safety, and quality of breathing air and medical air/gases, require analysis of breathing air on site through monitoring and testing for purity and quality by an independent, certified, accredited laboratory.

There is a growing need in the industry for accurate and dependable breathing air and gas purity monitoring, testing, and analyzing systems located at a provider's air compressor output ensuring the breathing air compressor provider facility breathing air produced receives analysis by an independent, certified, accredited laboratory to satisfy government and authorized safety agency requirements.

It is extremely important for safety that the quality of breathing air samples provided from an air compressor or storage tank are tested by accurately calibrated and validated gas purity sensors that receive a direct gas sample from the source of breathing air on site, so that the correct gas sample purity data can be collected and analyzed for proper testing, analysis, and accreditation.

The gas sample test and analysis housing must be very secure and free from access by unauthorized personnel that may disturb, intentionally or unintentionally, one or more gas sensors or the air sample intake manifold to the sensors.

Applicant's invention described herein provides a breathing air and gas monitoring, testing, and analyzing system and method that is embodied in a laboratory on location gas sample test system installed at a breathing air provider facility. The air/gas purity and quality data obtained in the laboratory on location can be collected and digitally stored and transmitted over the Internet to a remote certified testing laboratory for further analysis, quality and safety evaluation, and for accreditation of the breathing air in quality and purity. The independent certified testing laboratory maintains a cloud computing-based website that includes the breathing air provider's private air quality account for access around the clock by the breathing air provider. The invention also includes the capability of providing a monitoring alarm that can detect dangerous impurities and gases, turn off a provider's air compressor, and notify interested parties of the dangerous impurities by cell phone, smart phone or other digital communication device.

Applicant has U.S. Pat. Nos. 10,161,923 and 9,134,284 that describe breathing air and gas sample test and analyzing systems, the contents of which are incorporated by reference herein.

SUMMARY OF THE INVENTION

A breathing air quality gas monitoring, testing, and analyzing system that includes a laboratory on location gas test system, that collects gas sample data, on board at a breathing air provider's facility, and transfers the gas sample data over the internet for breathing air analysis by an independent, remote, accredited, and approved air quality monitoring facility.

The laboratory on location gas test system has three assemblies, that each provide a specific important gas sample sensor data collecting, monitoring, testing, gas purity data function, namely, 1) a secure chassis to protect the gas sample sensor and microprocessor equipment, 2) a "canary" gas sample test module, that is swappable, mounted inside of said secure chassis, and 3) a gas purity sensor data analysis, data communication device controller, mountable in or outside said secure chassis. Each assembly is described below.

1) A secure chassis, installed near or on board an air provider's air compressor system, that houses two major assemblies, the swappable "canary" gas sample testing and analyzing module and a gas sensor data microcontroller, having components for on-site continuous gas sample monitoring, testing, analysis and data security, an LCD display for gas sensor status information, and a gas inlet conduit in fluid communication with the provider's breathing air compressor outlet for gas samples of breathing air;

2) A "canary" gas sample testing and analyzing module (canary test module), removable (swappable) but securely mounted inside said secure chassis, that includes a plurality of different gas sample sensors that provide data signals to an onboard microcontroller, and sensor data communication output portals from the microcontroller and chassis for transmitting gas sample data from the "canary" test module; and 3) A gas sensor data internal and external communication controller, described below, for sensor data communication control with a communication computer tablet and mobile smart device and internal data communication with the "canary" test module and microcontroller for gas sensor data memory and transmitter. The gas sample data communication controller transmits gas sample data over the Internet for monitoring, analysis and approval at the remote independent testing and analysis monitoring accredited facility that can provide accredited breathing air analysis reports/certificates to the breathing air provider facility.

The chassis has a large storage area for internal batteries, external electric supply of AC voltage from a wall circuit, with battery backup in case of power failure. The chassis also has display lights, red and green, to indicate the status of the gas sample data intake devices and gas sensors and compressor shutdown.

The "canary" gas sample test module performs the gas sampling and data collection of the individual gas identity and concentration which is stored in the microcontroller to be transmitted to the independent laboratory for analysis. The gas analysis data can be transmitted from the microcontroller to an exterior communication device (controller) such as a tablet or laptop via Wi-Fi or an Ethernet portal in the "canary" gas sample module.

The "canary" test module utilizes a digital connection between the sample gas sensors and a microcontroller to facilitate the physical connection which facilitates command and control from software as firmware loaded into the microcontroller. The software checks the status of the sensors (present or not present), stores the serial number and model of the sensors and interrogates the sensors for a reading value representing the parts per million (or other measurement) of the selected gas sensor that is being sampled. This sample signal value is compared against the appropriate standard for safety purposes and transmitted from the microcontroller to an embedded computer database via digital connection for further processing and transmission ultimately to cloud-based software and to a remote monitoring accredited test and analysis facility.

The "canary" gas test module is mounted in a sealed, rigid container and removably detachable from the chassis. The "canary" test model has digital gas sensors attached on a board like structure and sample gas intake manifolds from the breathing air source for transfer to each gas sample sensor for physical contact with the gas sensors. Each gas sensor is connected to an electrical power source and a digital data storage site on the microcontroller for storing the essential gas sensor signal digital data. The microcontroller also has a computer program that can be used to analyze the correctness of each of the gas sensor sample signals to ensure that the gas sample is safe and does not contain impurities or dangerous improper gases.

The "canary" test module can be manually swapped out the laboratory on location test and analysis chassis and exchanged with an identical, canary test module to ensure accurate sensor calibration and safe operation at all times. Relatively quickly, an identical (or upgraded) "canary" test module unit can be replaced in the chassis. Each of the "canary" test modules has its own individual model and serial number that is unique so that the test unit can be tracked as to its calibration history and operational history. Each sensor can also be individually replaced. This enables the "canary" sensor module operation to ensure consistent, reliable, accurate values for safe breathing air or gas, resulting in accreditation by an independent test and monitoring facility.

The "canary" gas sample test analyzing module and its accuracy and dependability are enhanced for governmental and other safety organizations accreditation by pairing two identical gas sensors for one specific gas, such as O2 together, and a pair of two identical CO sensors paired together, for redundancy to ensure reliability and accuracy in each gas sample for oxygen and carbon monoxide. Redundancy could be applied to any and/or all sensors.

The laboratory on location (LOL) test system, in addition to the chassis and the "canary gas test module" inside the chassis, includes an exterior, internet communication device (controller), such as a laptop computer or tablet, that receives the stored digital (and analog) gas sample data from the "canary" test module microprocessor. The exterior internet communication device (controller) is for receiving and transmitting the gas sample sensor data, obtained from the "canary" gas sensor test module, over the Internet to the remote testing accreditation facility that monitors and analyzes the quality of breathing air with the gas sample sensor data being transmitted to its server. The exterior communication device (controller) can be a tablet, laptop computer, or smart phone/cell phone device that receives Wi-Fi or Ethernet signals from the "canary" gas sample test module microprocessor.

The independent accredited remote laboratory has a portal and website on the digital data cloud, in addition to its website on its server that includes accessible files for breathing air providers and for reading, receiving, and storing gas accreditation certificates for the breathing air of a provider facility. The independent, remote, accredited monitoring and test facility, in some embodiments, are responsible for providing the Laboratory on Location test module data, that must provide gas sample quality sensors that are extremely accurate and reliable for monitoring, analyzing, and approving or disapproving the quality of a provider's breathing air output system, such as a breathing air compressor.

Qualified personnel at the remote, independent accredited monitoring and testing facility receive the breathing air provider's gas sample sensor data for air quality analysis to conduct a pass or fail test of the quality of air. The remote, independent accredited monitoring and analysis facility has a bi-communication Internet link with the breathing air provider's facility personnel and the exterior communication device (controller) that communicates with the microprocessor in the "canary gas sample test module located in the chassis of the laboratory on location at the breathing air provider's facility to provide information to the provider concerning the quality of the provider's air output, pass or fail, which may include shutting down the air compressor at the providers facility. The provider can go on the Internet and access the provider's cloud-based account, set up and monitored by the accredited monitoring facility on a cloud portal, at any time, to obtain accreditation data or certificate for the provider's air that is produced by the provider.

The breathing air provider's air compressor system or hospital air providing system, in the event of an air purity failure, would be shut down.

In summary, using the laboratory on location LOL test system provided by Applicant can provide the accreditation necessary to the provider of breathing air from samples taken periodically or continuously when the air compressor is in operation, at the provider's facility. The Applicant's laboratory on location LOL test system can be permanently installed at the providers facility or can be a portable system for use as a one time survey at different providers' facilities.

It is an object of the invention to provide a breathing air laboratory on location at a breathing air provider facility that allows the breathing air of the provider to receive independent accreditation of the quality of the breathing air provider's output air continuously, when the air compressor is putting out breathing air, or periodically based on the operation of the provider's air production system.

Another object of the invention to provide a breathing air gas analysis system having redundant gas purity sensors for critical gases such as O2 and CO for safety and improved accuracy and quality during testing.

Still another object of the invention is to provide a breathing air gas purity analysis system that has a gas sensor array "canary" test module that can be removed and swapped for an identical (or updated) "canary" gas sample test module on site for enhanced accuracy, reliability, and quality for accreditation of the breathing air intake output of the provider on site. This also provides minimal down time between calibration and repairs.

In accordance with these and other objects that will become apparent hereinafter, the instant invention will now be described with particular reference to the company drawings.

DESCRIPTION OF THE PREFERRED EMBODIMENTS

Figure 1:
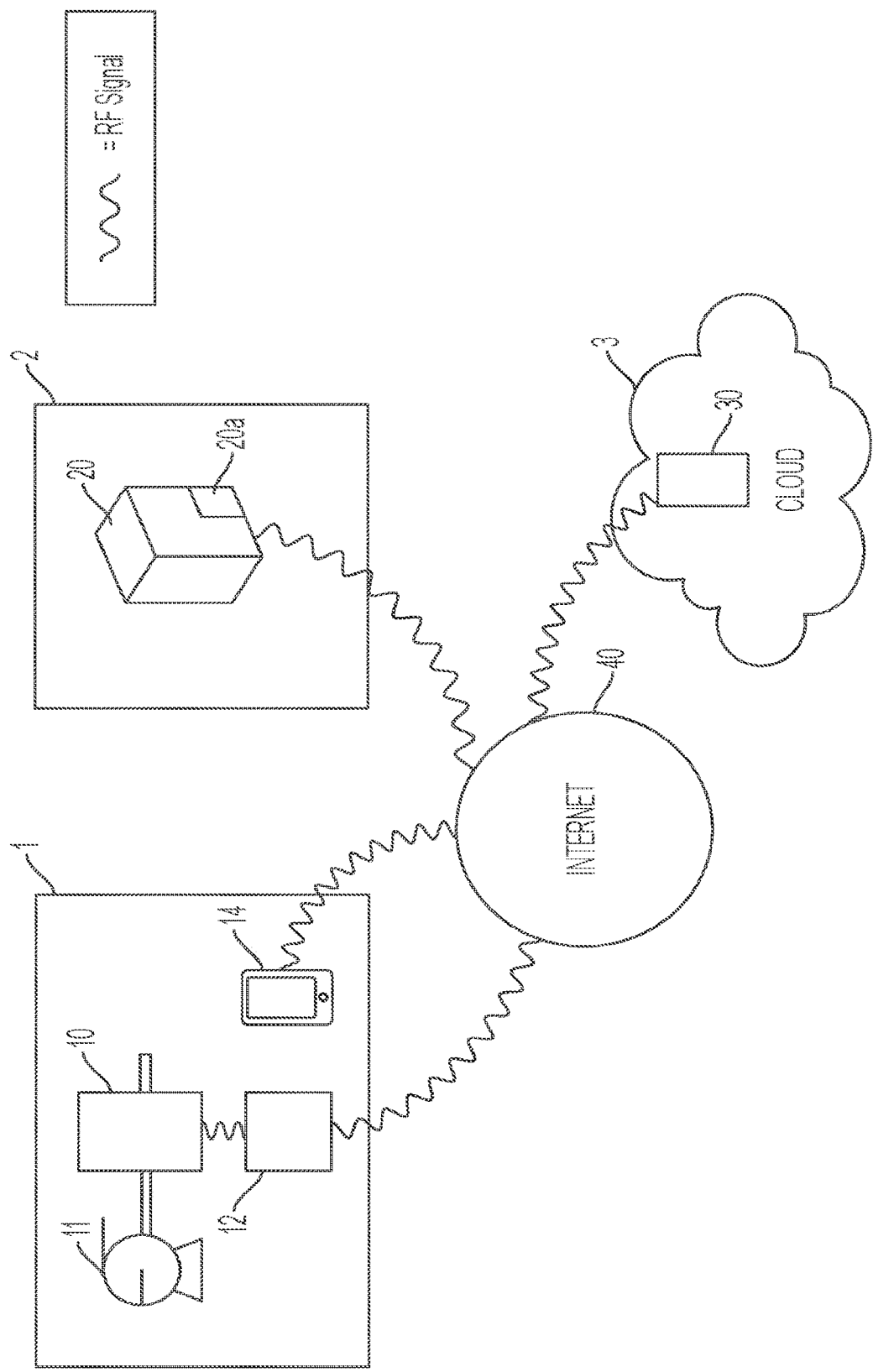
FIG. 1 is a schematic diagram of the Laboratory on Location test system, including major components that provide the gas sample test analyzing system for a breathing air provider accreditation.

FIG. 1 is a schematic diagram of the remote breathing air and gas test and analysis system, the laboratory on location (LOL), at the breathing air provider's facility 1. The LOL breathing air gas test system includes a breathing air and gas test module 10 connected in fluid communication to an air compressor breathing air gas source 11. Alternatively the gas test and analysis module 10 may be directly or portably, connected to a personnel breathing air tank as a medical air supply.

The LOL breathing air test analysis module 10 can be integrated into the breathing air provider's air compressor wherein breathing air purity and quality test and analysis are desired for accreditation of a breathing air provider's facility breathing air produced for users, such as breathing air for firemen, and other rescue people, breathing air for scuba divers, and medical institutions such as hospitals.

At the remote, accredited, independent breathing air gas quality certification monitoring facility 2, the overall breathing air accreditation system, embodying the invention, further includes the accredited facility server 20 maintained by the independent accredited test monitoring facility that includes a computer program 20a that can receive, store, and analyze air and gas sample sensors signal digital data sent from the breathing air provider's facility over the Internet 40 for sample gas purity and quality testing analysis and accreditation, if acceptable.

A bi-directional communication link between the breathing air test and analysis module 10 and gas sensor data controller and communication computer 12 located at the air provider facility 1 is established over the Internet 40 and transmitted to the independent remote accredited air-quality test facility 2 and its server 20 so that the independent accredited test facility to can receive air test and gas test analysis data from test and analysis module 10. The accredited monitoring facility 2 can also send communications to the breathing air provider's facility 1 concerning problems or failures, in order to stop or shutdown the air compressor 11 at breathing air provider's facility 1 in case of failure of the quality of breathing air compressor at any time. The gas sample test and analysis module 10 at the breathing air provider's facility 1 can also communicate over the Internet 40 with cloud-based 3 portal and website account 30 for the breathing air provider gas sample test results and breathing air accreditation documentation and sample analysis information that is provided and maintained by the gas certification monitoring center 2 that is responsible for breathing air accreditation analysis.

Personnel at the breathing air provider facility 1 can also access the Internet 40 at any time including the accredited air quality monitoring service facility 2 server 20, and the cloud 3, account portal 30 using a smart phone 14 or any computer with internet access in order to obtain, around the clock, breathing air purity, quality test and analysis data to ensure the continued quality and safety of output breathing air. Smart phone 14 can also be used to receive test sensor signal data from module 10 for real-time gas quality results, which could also include an alarm or a test failure notification. It is an important aspect of this invention that a breathing air provider can obtain 24/7 communications concerning the quality of its breathing air being produced and accreditation attesting to the quality of its breathing air whenever necessary.

Figure 2:
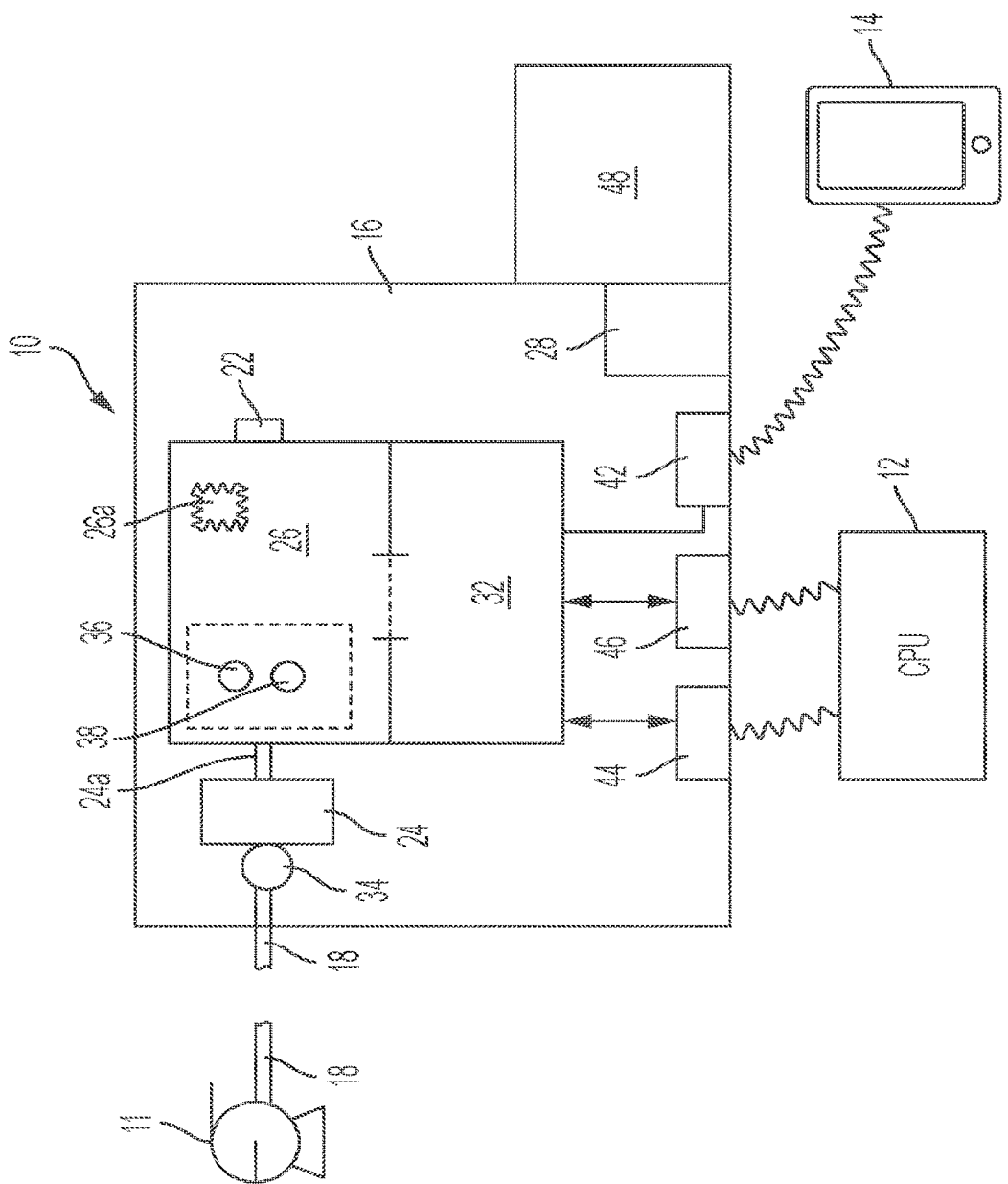
FIG. 2 is a schematic representation of the breathing air gas testing laboratory on location chassis, removable canary test module, and communication controller in one embodiment of the present invention.

FIG. 2 shows, as a schematic diagram, one embodiment of the gas test and analysis module 10, the present invention termed the Laboratory on Location (LOL) primarily because the LOL test system is located at the air provider's facility 1.

The LOL gas test and analysis module 10 includes a gas inlet breathing air inlet conduit 18 from breathing air source 11, typically a breathing air compressor.

The LOL test and analysis module 10 has a rigid, secure chassis 16, that in some embodiments, is a large rectangular, rigid enclosure, with sufficient internal space for hosting inlet air breathing conduit 18, inlet air valve 34, and inlet air conduit 24a from manifold 24 to provide air and individual gas samples to canary module 26. The gases to be tested by the gas sensors 36 and 38 located inside a swappable, removable canary gas sensor array module 26 are shown as an example in one embodiment.

The chassis 16 also contains an electric power unit 28 that is connectable to a building outlet power source or compressor power supply for electric power distribution to all gas test and analysis sensors, shown as examples 36 and 38, inside the canary test module 26. The canary test module 26 may be activated when the provider's air compressor is powered "ON". This may be accomplished by detecting a certain level of vibration or sound (dB) when the compressor equipment motor is powered ON. This would alleviate the necessity of having additional electrical wiring that turns on the canary test module each time the air pump is turned on and off. The canary test module would not have to be electrically connected directly to the power of the air compressor on and off switch. Power source 28 may also include backup battery power, in case of a building power failure.

Rigid chassis 16 may also contain two or more status lights configured to show incoming power status, communication status, and impurity alarm status lights that would include a greenlight, if the gas composition is of usable quality, and a red light for unusable unhealthy levels of impurities that are detected in any sample gases.

The gas sample inlet manifold 24 is represented schematically, but there are in fact two or more manifolds integrated with and into the canary test module 26, in fluid communication with the gas sample inlet 18, connected to the breathing air source 11 to provide gas samples to the all the gas sensors, including sensors 36 and 38, (whenever the compressor 11 is on, as determined by valve 34), that can be tested and analyzed continuously during air compressor 11 operation, or periodically as desired by the breathing air provider. Each of the gas sample inlets include appropriate gas line fittings, as are known in the art, and are compatible with the fittings of the gas source 11 respectively. Inlet conduit 18 and outlet 22 may also include valves, operable to open and close the inlet 18 and outlet 22, when the air compressor is turned on and off. An electronic gas sample flow detector 34 is in fluid communication with inlet 18 and adapted to detect a change in pressure, flow rate, and/or temperature such that the gas test and data collecting module 10 can be activated immediately when sample gases are introduced into the module 26, when the air compressor 11 is on, rather than rely on a user to manually activate the gas test and data collecting module 10.

One or more gas sensors 36 and 38, as examples, contained in the canary gas sample test (sensor array) module 26 are in fluid communication with the gas passages in manifolds 24. In some embodiments, the gas sensors 36 and 38 are electronic, UV, or ionic gas sensors capable of generating electronic signals based on various gas impurity characteristics. In some embodiments, the gas sensor electronic signal corresponds to a voltage or electronic potential. The gas sensors 36 and 38 can be calibrated to identify a gas, its concentration, and detect virtually any type of gas impurity. The following is a non-exhaustive list of gases and impurities the present invention is capable of detecting and analyzing. The device can monitoring test breathing air or other breathing gases, such as oxygen only. This list is illustrative only and used set forth here merely to give a broad understanding of some of the sample gases that are recognized:

Analytes
   Carbon Dioxide $CO_2$
   Carbon Monoxide CO
   Hydrocarbons
   Water Vapor
   Nitric Oxide NO
   Halogenated Solvents
   Acetylene
   Halogenated Hydrocarbons
   Oil and Particles
   Oxygen $O_2$
   Nitrogen Dioxide
   Odor The gas sensors (including sensors 36 and 38) are mounted on the main sensor board 26a in the canary gas sample test (sensor array) module 26 and are electrically coupled to send sensor data signals to microcontroller 32 that includes the necessary electronic and computer firmware components to receive gas data purity electronic signals from each of the sensors. Canary gas sample test (sensor array) module 26, that houses a main gas sensor board 26a, containing an array of gas sensors, is given a unique serial number and model number identification so that the canary test module 26 can be physically removed from the chassis 16 as a unit and swapped out, and replaced with an identical (or updated) canary gas sample test (sensor array) module 26 unit, to ensure that all the sample gas test sensors are operating correctly and accurately.

The microcontroller 32, connected to and within the gas test and data collecting module 26, is also connected to an ethernet port 44, cell phone modem 42, and Wi-Fi output 46 for communication of sample gas sensor signal data collected and stored by the microcontroller 32 to be communicated and transferred to the Internet 40 (FIG. 1), communication controller CPU 12, for transfer to the server 20 at the gas sample validation and monitoring center, to for laboratory analysis to determine if the tested gas samples pass or fail quality, safety and purity for validation and accreditation of the breathing air produced by the provider air compressor equipment.

The canary test and data collecting module 26 contains independently mounted sensor boards along with the microcontroller 26 command board for easy replacement of a single sensor when needed. Certain sensors are mounted within a central manifold 24 and other sensors are independently mounted such as $H_2O$, particle, oil vapor, vacuum for ambient and flow sensor. In some embodiments there is a breathing air board testing sensor module as part of the standard unit and an optional medical board sensor for clients requiring testing of medical air standards.

The canary gas sample test module 26 forms many functions including checking that there is an appropriate gas flow before engaging a sensor; check for particulates to ensure that it passes the test before engaging the gas sensors; check for oil vapor to ensure it passes the test before engaging the gas sensors; check for $H_2O$ to ensure it passes the vapor test before engaging the gas sensor; and get data from each gas sensor that is needed for aa validation and accreditation test and check these values against safety standards at the independent gas validation and monitoring center 2 and send the gas sample test data over a secure hidden Wi-Fi ethernet or cell modem to the master communication controller CPU 12.

The secure chassis includes an LCD display 48 mounted to the chassis for displaying valuable information such as various warning displays that the "canary" test module is not present; delay testing for various reasons including battery and warm-up; controller connection to the cloud is lost; and validation required or other important information regarding the sample gas testing.

The main communication controller CPU 12 (shown in FIG. 2) can be a computer desktop, or laptop computer that is positioned adjacent chassis 16 and connects to an ethernet portal 44 or Wi-Fi communication 46 to provide command and control of the gas test and data collecting module 10 functions. The main communication controller CPU 12 can also transmit essential sensor gas purification data over the Internet 40 to server 20 at the gas validation monitoring center 2 for pass or fail and accreditation and server 20 can notify and the cloud-based portal 30.

Figure 3:
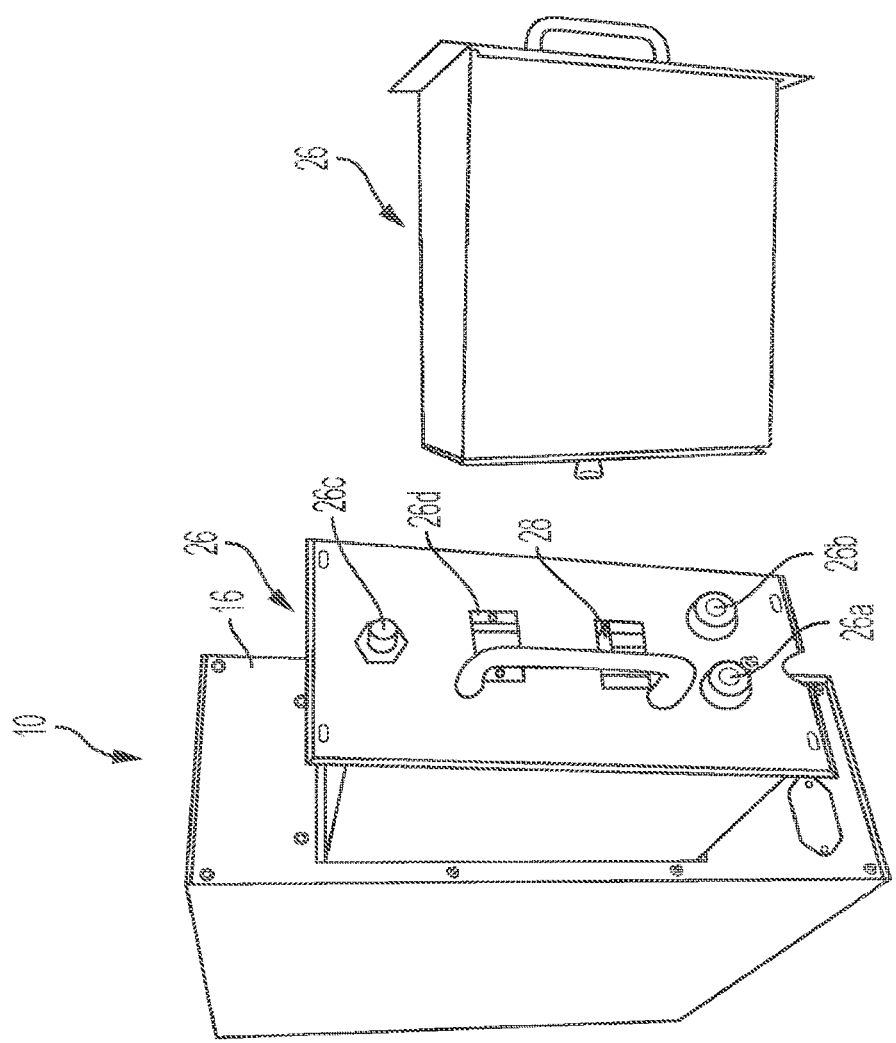
FIG. 3A and FIG. 3B show the Laboratory on Location chassis and swappable canary test module housing removed from the chassis.

FIG. 3A shows the laboratory on location test and data collecting module 10 including the rectangular rigid chassis 16 that includes the "canary" test module 26 that is swappable and removable by a handle 28 from the chassis 16.

FIG. 3B shows the "canary" test module 26 completely removed from chassis 16. Each "canary" test module 26 has its own individual unique serial number and model number, as do all the sample gas sensors contained therein, for complete tracking of the accuracy and dependability of all the sensors in the system. Note that the "canary" test module 26 is itself securely enclosed on all six sides to prevent unauthorized access to any of the sensors and microprocessor equipment inside to guarantee the accuracy of the sensors and microprocessor being utilized. Especially the unit is secure from unauthorized personnel at the breathing air provider's facility where the air compressor output for breathing air is being tested. The canary test module 26 can be removed by authorized persons securely with a key and lock for annual, periodic, or necessary maintenance and returned to the remote monitoring, test and validation accredited laboratory for complete reconditioning of all the sample gas sensors and microprocessor units contained therein. By swapping out the canary gas sample test module 26, obtaining accurate test results at the breathing air provider's facility is not in any way disrupted, because another identical (or updated) canary gas sample test module 26 will be inserted and into chassis 16, after the previously existing canary test module has been removed.

FIG. 3A, the "canary" gas sample test module 26 includes, on the front panel air inlet 26a, validation gas inlet 26b, a relay 26c that can turn the compressor system on and off, or any other alarm use, based on the gas pressure, and a handle 28 used to withdraw the unit "canary" gas sample test module 26 from the chassis 16 swapped out.

Figure 4:
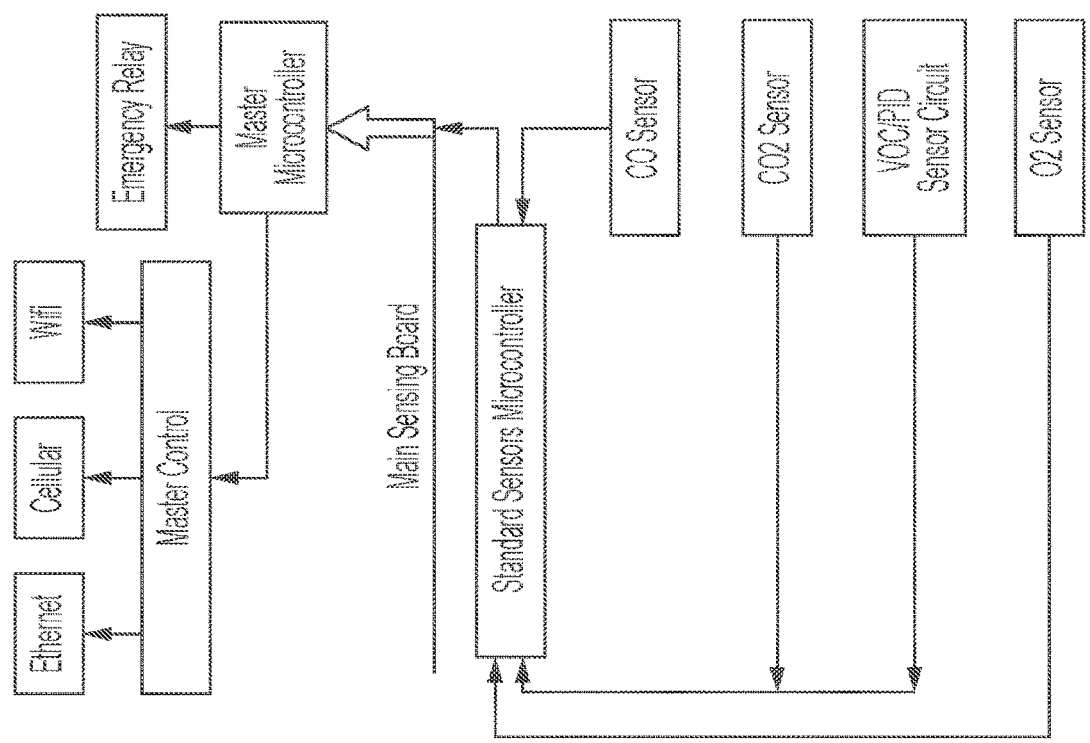
FIG. 4 is a block circuit diagram of the canary sensor array that is removable and swappable from the LOL test chassis.

FIG. 4 shows a schematic electronic circuit diagram of an array of sample gas sensors on a main sensing board that includes a CO sensor, a CO2 sensor, a VOCs/PID sensor circuit and an O2 sensor, all connected to the Standard Sensors Microcontroller. The CO and O2 sensors may include two redundant sensors, which are explained below, as to the CO and O2 redundant sensors with respect to FIG. 5.

The standard sensors microcontroller is connected to a master controller where the sample gas data signals from the sensors are entered into a processor that can monitor and process the sensor signals in accordance with standards for sample gas quality and purity.

The Master Microcontroller is connected to an emergency relay to stop the system in the event of dangerous, impure air being produced. The Master Control is connected to output ports that include the ethernet, cellular modem, and Wi-Fi for transmitting sample gas sensor data to the communication controller CPU 12 (FIG. 1) that connects to the Internet and to the cloud-based portal and account. The sample gas sensor main sensing board shown in FIG. 4 constitutes the major layout in the "canary" gas sample test module 26 that are fixed inside the module 26 that can be exchanged by swapping out canary module 26 inside chassis 16.

Redundant O2 and Co Sensors (and Others)

Figure 5:
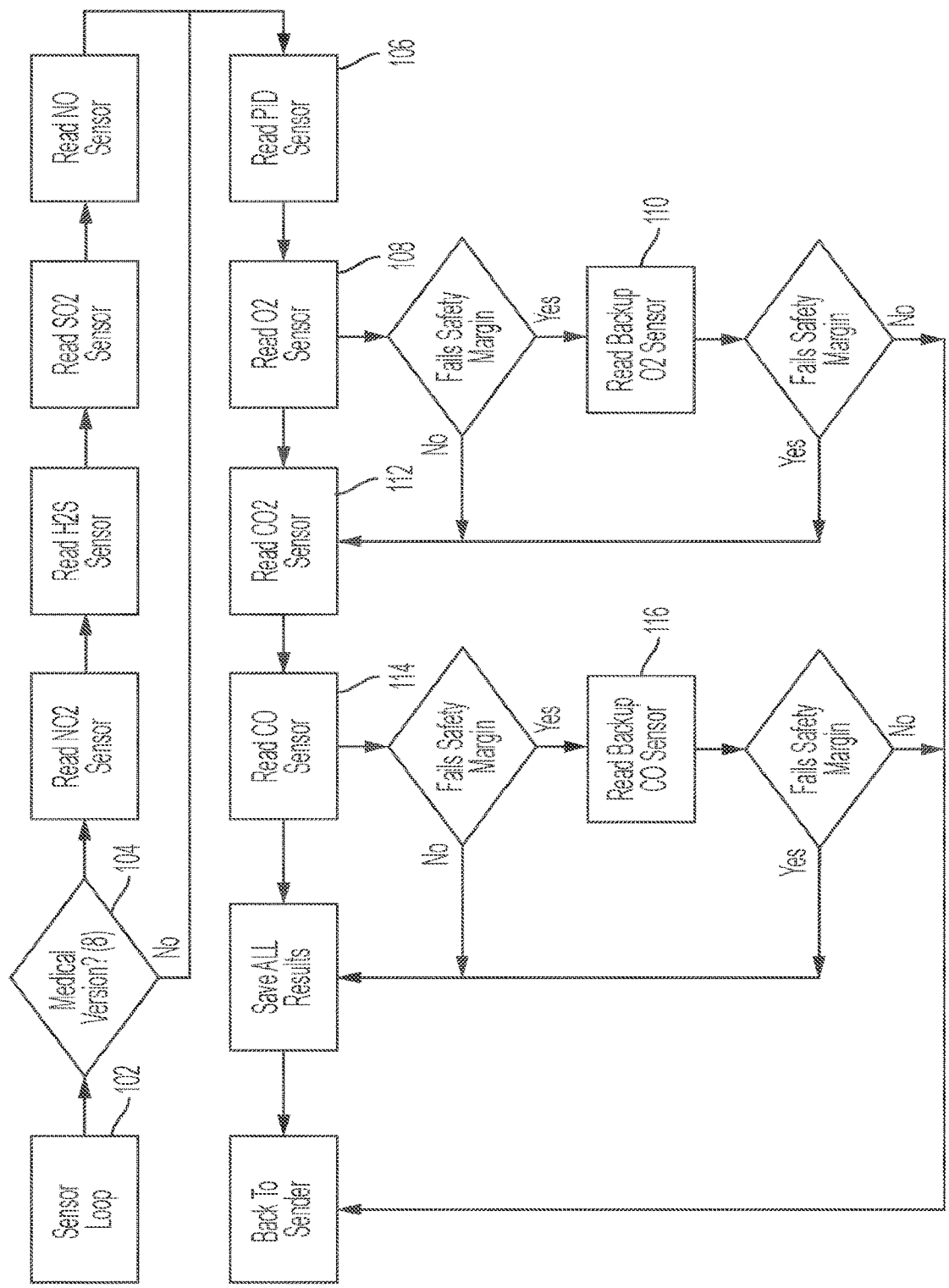
FIG. 5 is a flowchart, block, electrical circuit diagram depicting the O2 and CO redundant (two identical sensors for one gas sample) gas sensor operation.

FIG. 5 shows a schematic flow diagram that shows the use of two identical gas sample O2 sensors, in gas flow series, in the canary test module 26 sensor mainboard, in order to ensure accurate testing of O2 by redundancy. The breathing air quality of O2 is critically important in the sensing test for the safety of users.

At sensor loop 102, if a gas sample were directed over an array of gas sensors shown, the output signal of each sensor connected to the sensor microcontroller is utilized. Referring to FIG. 5, the gas sensor output program begins at sensor loop 102, a gas sample is directed to start at both the main sensing board and/or the medical sensing board 104. If the optional medical sensor board is not selected, as in this example, the flow indicates "NO" in the sample gas flow to the main sensor board.

The main sensor board is read at the PID sensor 106. The first O2 sensor 108 sends a signal that either passes, allowing the signal to transfer to the next sensor reading CO2, or fails a safety margin. If the O2 sensor 108 first in line fails the safety margin, then the backup O2 sensor 110 signal is read. If the first O2 sensor read passes the safety margin, which is a NO to the failed safety margin criteria, then the program continues to read the next CO2 sensor. If the backup O2 sensor fails the safety margin, then the O2 sensor signal reverts back to the sender, which will indicate a sensor O2 failure and the sample gas test. If the backup O2 sensor passes the safety margin, the program then directs the CO2 sensor to be read, second. After the first sensor signal passes the O2 sensor signal passes the safety margin, the gas sample goes next to the CO2 sensor 112.

The same sensor redundancy is used for testing the sample gas CO carbon monoxide. The gas sample is passed and read sequentially at the first CO sensor 114. If the gas sample passes the safety margin for CO2, the data is passed to all results and back to the center. If the CO2 fails the safety margin test at 114, the gas sample is read at a second back up CO sensor 116. If the gas sample fails to back up CO sensor 116, the failure data is passed to the sender, aborting the test. Again the CO sensor redundancy greatly improves the accuracy, dependably, and ability of the test the analysis module system for accreditation of breathing air safety.

The redundancy use of any other gas sensor or sensors, described in the invention and system used herein, can also be provided for use in the "canary" test module for increased accuracy and reliability of system safety results.

At the remote monitoring and gas sample sensor analyzing center 2 (FIG. 1), a qualified representative receives the breathing air gas impurity data and compares the impurity data to a known, pre-existing list of gas impurity threshold values to determine if a specific breathing air gas impurity level has been exceeded and/or to determine if the breathing air gas sample passes one or more gas purity requirements for certification and the provider's breathing air can be and receive accreditation. The results of the comparison tests are then determined, the information stored in the name of the breathing air provider facility, and the test results sent back to the breathing air provider facility 1 and/or to an individual, along with validation and accreditation of the breathing air, if available. The accredited monitoring center 2 would also send the validation and accreditation documentation to the cloud 3 that contains the breathing air provider's breathing air test quality account information, stored under the name of the breathing air provider on the cloud portal account 30, thereby allowing the breathing air provider and people at that facility 1 to access the cloud at any time in order to receive breathing air validation and accreditation of the provider's breathing air.

The instant invention is been shown and described herein in what is considered to be the most practical and preferred embodiment. It is recognized, however, that departures may be made therefrom within the scope of the invention and that obvious modifications will occur to a person skilled in the art.

The invention claimed is:

1. A gas sample analysis system for analyzing and certifying a gas supplied by a gas source for breathable consumption, the system comprising:
  a chassis located at a first location, the chassis having an inlet configured to receive a gas sample of the gas, the chassis having a communication controller central processing unit (CPU) configured for receiving and transmitting sensor data on a network;
  an analysis module removably couplable for insertion into the chassis, the analysis module communicatively coupled to the communication controller CPU while the analysis module is coupled to the chassis, the analysis module including:
    a first gas sensor and a second gas sensor in fluid communication with the inlet, the second gas sensor identical to the first gas sensor, the first gas sensor and the second gas sensor configured to receive the gas sample and transmit data signals that correlate to one or more gas concentrations of the gas sample,
  a controller communicatively coupled to the first gas sensor and the second gas sensor to receive the data signals, the controller including firmware and data processing software for determining and comparing the results of the data signals, the controller configured to transmit results of the data signals as sensor data to the communication controller; and
  a server computer located at a second location remote from the first location and communicatively coupled to the communication controller CPU via the network, the server computer configured to receive the sensor data from the communication controller, compare the sensor data to one or more gas purity threshold parameters, and determine if the gas supplied by the gas source passes one or more gas purity requirements for certification based on the sample gas,
  wherein the analysis module is configured to power on in response to detecting activation of an air compressor associated with the gas source, the analysis module configured to detect activation of the air compressor by detecting a level of vibration or sound that exceeds a threshold level, the vibration or sound associated with activation of the air compressor, and
  wherein, responsive to a determination that the gas supplied by the gas source fails one or more gas purity requirements, the server computer transmits instructions to disable the air compressor of the gas source from supplying the gas for breathable consumption.

2. The system of claim 1, wherein the analysis module further comprises a relay configured to turn off the gas source responsive to the controller receiving the instructions configured to disable the gas source from the server computer.

3. The system according to claim 1, wherein the server computer is configured to store the sensor data.

4. The system according to claim 1, wherein the gas source is an air compressor, a pipeline of breathing air of a facility, one or more air tanks, a hospital air supply, or ambient air.

5. The system according to claim 1, wherein the gas is breathing air or other pure air for fireman breathing air, diver breathing air, industrial clean-air, or medical breathing air.

6. The system according to claim 1, wherein the analysis module is configured to detect activation of the air compressor based on a gas flow detector that is in fluid communication with the inlet, the gas flow detector configured to detect a change in pressure, a change in flow rate, or a change in temperature.

7. The system according to claim 1, wherein the first gas sensor and the second gas sensor are configured to detect concentrations of carbon dioxide (CO2), carbon monoxide (CO), hydrocarbons, water vapor, nitric oxide (NO), halogenated solvents, acetylene, halogenated hydrocarbons, oil and particles, oxygen (O2), nitrogen dioxide, or odors.

8. The system according to claim 1, wherein the analysis module, the first gas sensor, and the second gas sensor each have a corresponding unique serial number and model number.

9. The system of claim 1, the analysis module further comprising one or more sensors in fluid communication with the inlet configured to test gas flow of the gas and test concentrations of particulates, oil vapor, or water vapor prior to activation of the first gas sensor and the second gas sensor.

10. A gas sample analysis module for analyzing and certifying a gas supplied by a gas source for breathable consumption, the module comprising:
  a module frame configured to be removably couplable for insertion into a chassis;
  an inlet disposed on a surface of the module frame, the inlet configured to receive a gas sample from a gas source;
  a first O2 purity test sensor and a second O2 purity test sensor in fluid communication with the inlet; and
  a controller configured to receive data signals from the first O2 purity test sensor and the second O2 purity test sensor, the controller including firmware and processing data software for determining and comparing the results of data received from the first O2 purity test sensor and the second O2 purity test sensor for air/gas quality assurance of the gas sample,
  wherein the gas sample analysis module is configured to power on in response to detecting activation of an air compressor associated with the gas source, the gas sample analysis module configured to detect activation of the air compressor by detecting a level of vibration or sound that exceeds a threshold level, the vibration or sound associated with activation of the air compressor, and
  wherein, responsive to a determination that the gas supplied by the gas source fails one or more gas purity requirements, the controller transmits instructions to disable the air compressor of the gas source from supplying the gas for breathable consumption.

11. A gas sample analysis module for analyzing and certifying a gas supplied by a gas source for breathable consumption, the module comprising:
  a module frame configured to be removably couplable for insertion into a chassis;
  an inlet disposed on a surface of the module frame, the inlet configured to receive a gas sample from a gas source;
  a first gas sensor and a second gas sensor in fluid communication with the inlet, the second gas sensor identical to the first gas sensor, the first gas sensor and the second gas sensor configured to receive the gas sample and transmit data signals that correlate to one or more gas concentrations of the gas sample; and
  a controller communicatively coupled to the first gas sensor and the second gas sensor to receive the data signals, the controller including firmware and data processing software for determining and comparing the results of the data signals, the controller configured to transmit results of the data signals as sensor data to a communication controller,
  wherein the analysis module is configured to power on in response to detecting activation of an air compressor associated with the gas source, the analysis module configured to detect activation of the air compressor by detecting a level of vibration or sound that exceeds a threshold level, the vibration or sound associated with activation of the air compressor, and
  wherein, responsive to a determination that the gas supplied by the gas source fails one or more gas purity requirements, the controller transmits instructions to disable the air compressor of the gas source from supplying the gas for breathable consumption.

12. The module of claim 11, wherein the analysis module further comprises a relay configured to turn off the gas source.

13. The module of claim 11, wherein the analysis module is configured to detect activation of the air compressor based on a gas flow detector that is in fluid communication with the inlet, the gas flow detector configured to detect a change in pressure, a change in flow rate, or a change in temperature.

14. The module of claim 11, wherein the first gas sensor and the second gas sensor are configured to detect concentrations of carbon dioxide ($CO_2$), carbon monoxide (CO), hydrocarbons, water vapor, nitric oxide (NO), halogenated solvents, acetylene, halogenated hydrocarbons, oil and particles, oxygen ($O_2$), nitrogen dioxide, or odors.

15. The module of claim 11, the analysis module further comprising one or more sensors in fluid communication with the inlet configured to test gas flow of the gas and test concentrations of particulates, oil vapor, or water vapor prior to activation of the first gas sensor and the second gas sensor.

* * * * *